United States Patent [19]

Baldwin

[11] Patent Number: 5,472,853

[45] Date of Patent: Dec. 5, 1995

[54] ENZYMATIC PROCESS FOR CEPHALOSPORINS

[75] Inventor: Jack E. Baldwin, Headington, England

[73] Assignee: University of Oxford, Oxford, England

[21] Appl. No.: 79,224

[22] Filed: Jun. 18, 1993

Related U.S. Application Data

[63] Continuation of Ser. No. 821,259, Jan. 10, 1992, abandoned, which is a continuation of Ser. No. 380,831, Jul. 17, 1989, abandoned, which is a continuation of Ser. No. 856,993, Apr. 29, 1986, abandoned.

[51] Int. Cl.$^6$ .................................................. C12P 35/00
[52] U.S. Cl. ........................... 435/47; 435/43; 435/183; 435/911
[58] Field of Search ............................ 435/43, 47, 183, 435/911, 171

[56] References Cited

PUBLICATIONS

ATCC Catalogue of Fungi, 1991, p. 5.
Luengo et al., Biotechnology, vol. 4, pp. 44–47, 1986.
Baldwin, *S. Chem Soc. Chem. Comm.* (17), 1984, pp. 1167–1170.
Baldwin et al., *Tetrahedron*, vol. 38, pp. 2773–2776, 1982.

*Primary Examiner*—Irene Marx
*Attorney, Agent, or Firm*—Janet T. McClain

[57] ABSTRACT

N-Terminal β,γ-didehydrovaline di- and tri-peptides are reacted with isopenicillin N synthetase to form 3-exomethylenecepham-4-carboxylic acids, e.g., δ-(L-α-aminoadipoyl)-L-cysteinyl-D-β,γ-didehydrovaline is incubated with the purified enzyme to provide 7β-(L-α-aminoadipoylamino)-3-exomethylenecepham-4-carboxylic acid. The 3-exocepham products are useful intermediates to 3-alkoxy-3-cephem and the 3-halo-3-cephem antibiotics.

4 Claims, No Drawings

ENZYMATIC PROCESS FOR CEPHALOSPORINS

This application is a continuation of application Ser. No. 07/821,259, filed on Jan. 10, 1992 now abandoned, which is a continuation of prior application Ser. No. 07/380,831 filed on Jul. 17, 1989, now abandoned, which is a continuation of prior application Ser. No. 06/856,993, filed on Apr. 29, 1986, now abandoned.

BACKGROUND OF THE INVENTION

This invention relates to a process for preparing cephalosporin compounds. In particular, it relates to an enzymatic process for converting certain peptides to 3-exomethylenecepham-4-carboxylic acids comprising the use of isopenicillin N synthetase (IPNS).

3-Exomethylenecepham-4-carboxylic acids and esters thereof represented by the following general formula are known.

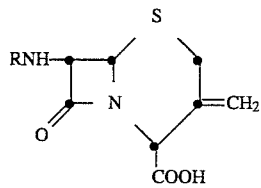

R = H or acyl

For example, Chauvette et al., *J. Org. Chem.*, 38, 2944 (1973) describe several 7-acylamino-3-exo-methyl-enecepham-4-carboxylic acids and esters as well as the 3-exomethylenecepham nucleus, 7-amino-3-exo-methyl-enecepham-4-carboxylic acid. U.S. Pat. No. 3,932,393, issued Jan. 13, 1976, describes a reductive process for preparing 3-exomethylenecepham compounds, in particular, the 3-exomethylenecepham nucleus.

3-Exomethylenecepham compounds are useful intermediates to 3-methyl-3-cephems, e.g., cephalexin, U.S. Pat. No. 3,507,861; to 3-halo-3-cephems, e.g., cefaclor, U.S. Pat. No. 3,925,372; and to 3-hydroxy- and 3-alkoxy-3-cephems described by U.S. Pat. No. 3,917,588.

Prior to this invention, the 3-exomethylene-cepham compounds were obtained by chemical synthesis. Owing to the importance of these cephalosporins as intermediates to clinically useful antibiotics, an alternative process for their preparation is highly desirable.

The cyclase isopenicillin N synthetase (IPNS) is well known for its ability to cyclize δ-(L-α-amino-adipoyl)-L-cysteinyl-D-valine to isopenicillin N via cell-free extracts of the enzyme from *Acremonium crysogenum* as well as other sources. Recent studies carried out with the purified enzyme have shown that the enzyme is capable of forming the cepham ring as well as the penam ring, J. E. Baldwin et al., *J. Chem. Soc., Chem. Commun.*, 1984, 1211. Because of the importance of the penicillins and cephalosporins in therapy, considerable effort has been undertaken to explore the use of IPNS in the preparation of β-lactam compounds.

SUMMARY

The tripeptides, δ-(L-α-aminoadipoyl)-L-cysteinyl-D-β,γ-didehydrovaline and δ-(L-carboxymethyl-cysteinyl)-L-cysteinyl -D-β,γ-didehydrovaline, and the dipeptides, phenoxyacetyl-L-cysteinyl-D-β,γ-didehydrovaline and phenylacetyl-L-cysteinyl-D-β,γ-didehydrovaline, are incubated with isopenicillin N synthetase to provide 7β-(L-α-aminoadipoylamino)-3-exomethylenecepham-4-carboxylic acid, 7β-[(L)-[(2-amino-2-carboxy)ethylthio]acetamido]-3-exomethylenecepham-4-carboxylic acid, 7-phenoxyacetylamino-3-exomethylenecepham-4-carboxylic acid and 7-phenylacetylamino-3-exomethylenecepham-4carboxylic acid.

The 3-exomethylenecepham products can be N-deacylated to provide the 7β-amino-3-exomethylene-cepham-4-carboxylic acid nucleus or an ester thereof and the nucleus converted by known methods to the desired 3-cephem antibiotic compound.

DETAILED DESCRIPTION

According to the process of this invention, an N-terminal didehydrovaline di- or tripeptide represented by the formula 1

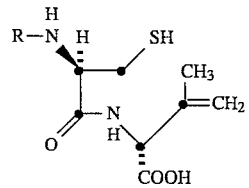

wherein R is phenylacetyl, phenoxyacetyl, or a group represented by the formula

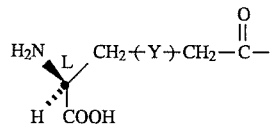

wherein Y is $CH_2$ or S, or an alkali or alkaline earth metal salt thereof, is reacted at a temperature between about 20° C. and about 40° C. with isopenicillin N synthetase in an aqueous environment at a pH of between about 6 and about 9 to form a 3-exomethylenecepham-4-carboxylic acid represented by the formula

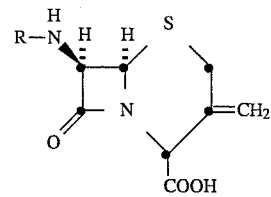

wherein R has the same meanings as defined above, or an alkali metal or alkaline earth metal salt thereof.

Alkali metal salts are, for example, the sodium or potassium salts while alkaline earth metal salts are, for example, the calcium or magnesium salts.

The enzyme employed in the process can be obtained from numerous sources including *Aeremonium crysogenum*, such as *A. crysogenium* ATCC 48272 and ATCC 36225, *Penicillium chrysogenum, Aspergillus nidulans, Streptomyces lipmanisi*, ATCC 27357, and *Streptomyces clavuligerus* ATCC 27064. The enzyme can be used in the form of a cell-free extract in a semi-purified form or, preferably, as the purified enzyme, e.g., prepared as described by Pang et al, *Biochem. J.* (1984), 222, 789–795, and J. E. Baldwin et al., FEBS LETTER, 1985, 188, 253. A preferred source of the enzyme is *Acremonium chrysogenum*, which has been deposited in the American Type Culture Collection where it is assigned the accession number ATCC 74315.

The substrates are prepared by known methods and are obtained in the stabile disulfide form. The tripeptide, δ-(L-α-aminoadipoyl)-L-cysteinyl-D-β,γ-didehydrovaline, (formula 1, $Y=CH_2$), is prepared according to the method of J. E. Baldwin et al., *Tetrahedron,* 1982, 18, 2776. According to the method, the benzyloxycarbonyl (CBz) and S-benzyl-protected dibenzyl ester, δ-(L-5-benzyloxycarbonylamino-5-benzyl-oxycarbonyladipoyl)-L-(S-benzylcysteinyl)-D-β,γ-didehydrovaline benzyl ester is deprotected by reduction with sodium-liquid ammonia to provide the tripeptide in the free thiol form. The thiol is oxidized rapidly to the disulfide by increasing the pH of the solution to 8.5 while passing oxygen through the solution.

The tripeptide, δ-(L-carboxymethylcysteinyl)-L-cysteinyl-D-β,γ-didehydrovaline, (formula 1, Y=S) is prepared by coupling S-trityl or (S-benzyl)-L-cysteinyl-D-β,γ-didehydrovaline benzyl or benzhydryl ester with N-CBz protected L-carboxymethylcysteine-α-benzyl ester.

The dipeptide substrates, phenoxyacetyl-L-cysteinyl-D-β,γ-didehydrovaline and phenylacetyl-L-cysteinyl-D-β,γ-didehydrovaline are prepared by N-acylation of S-benzyl-L-cysteinyl-D-β,γ-didehydrovaline benzhydryl ester or with the dipeptide having like known protecting groups for the carboxy and sulfhydryl groups of the dipeptide.

Prior to contacting the substrate with the IPNS enzyme, the disulfide form is reduced in solution to the thiol form with a suitable reducing agent such as dithiothreitol, β-mercaptoethanol or glutathione.

The process is carried out in the presence of ferrous ion and L-ascorbic acid. With these cofactors present, the IPNS enzyme, which functions as an oxidase, provides its maximum activity. The minimum amount of ferrous ion required to activate the enzyme is generally used in the process. In general, the concentration of the ferrous ion is between about 50 μM to about 0.2 mM. The higher the purity of the IPNS enzyme, the lower the amount of ferrous ion required. Conversely with impure enzyme, larger amounts of ferrous ion are required for activation. The ferrous ion is used in conjunction with ascorbic acid and usually the two cofactors are used in about equal concentrations. Sources of ferrous ion include, e.g., the salts, ferrous sulfate, ferrous chloride, ferrous carbonate, or other suitable salt.

During the process, hydrogen peroxide can be generated. To avoid the presence of excess levels of peroxide, which may be deleterious to the enzyme, substrate, or product, a catalase such as beef liver catalase is added to the incubation mixture.

The process is carried out in the presence of oxygen and with agitation by shaking or stirring. When carried out on a large scale such as in a large tank or flask, the incubation mixture may be aerated by passing a stream of air through the incubation mixture with vigorous agitation.

The incubation mixture can be maintained at the desired pH of between about 6 and about 9 with a buffer. Suitable buffers include ammonium bicarbonate, tris buffer, and MOPS (3-[N-morpholino]propanesulfonic acid). The amount of buffer incorporated in the mixture is generally in excess of the molar amount of the di- or tripeptide substrate used. Preferably, the process is carried out at a pH of between 7.5 and about 8.5.

The di- or tripeptide substrate is generally employed at a concentration of between about 0.1 mM to about 5 mM, although higher concentrations are not prohibited. As with other enzymatic processes, the substrate should be relatively pure and free of heavy metal contamination. Such metals can inhibit the enzyme entirely or drastically reduce its activity.

The IPNS enzyme is used in large excess relative to the substrate for best results. The activity of the enzyme is expressed in terms of units of activity. One unit of activity is the amount of enzyme required to form 1 μmol of isopenicillin N per minute with (L-α-amino-δ-adipoyl)-L-cysteinyl-D-valine in the assay described by Pang et al., supra. When carrying out the process with high concentrations of substrate and a large excess of enzyme, it may be beneficial to introduce oxygen into the incubation mixture during the process.

The process proceeds rapidly when purified enzyme is used in excess with substrate of high purity. In general, the process can be carried out from about 10 minutes to about 2 hours and, preferably, is allowed to proceed for 45 minutes to one hour. It will be appreciated that with large scale incubations of enzyme and substrate, somewhat longer times may be required than with smaller scale reactions.

The process is terminated by the addition of a solvent such as acetone to the incubation mixture. The precipitated protein is separated, e.g., by centrifugation, and the product is isolated from the supernatant by conventional means. For example, the supernatant can be lyophilized and the product isolated from the lyophile by chromatography such as by reverse phase octadecylsilane HPLC. Alternatively, the product may be isolated by extraction from the incubation mixture after separation of protein.

In a preferred embodiment of the process, a tripeptide represented by the formula

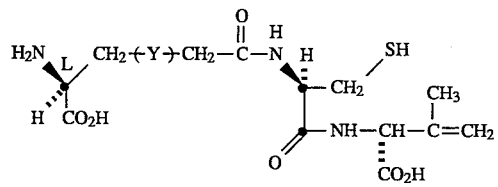

is incubated with excess purified IPNS as described above to provide the 3-exomethylenecepham-4-carboxylic acid represented by the formula

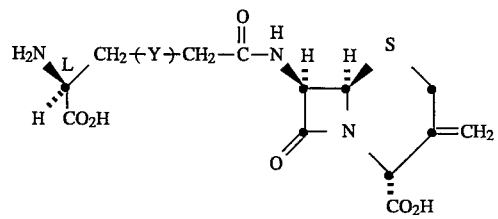

An especially preferred embodiment of this invention comprises incubating the tripeptide, δ-(L-α-aminoadipoyl)-L-cysteinyl-D-β,γ-didehydrovaline with excess IPNS in purified form by the procedures described hereinabove.

The 3-exomethylenecepham-4-carboxylic acids provided by the process are useful intermediates to known 3-alkoxy-3-cephem and 3-halo-3-cephem antibiotics. For example, the products can be N-deacylated by the method described by U.S. Pat. No. 3,697,515 to provide the 3-exomethylenecepham nucleus described by U.S. Pat. No. 3,932,393 and represented by the formula The 3-exo nucleus can be converted to the 3-methoxy-3-cephem antibiotics by procedures described by U.S. Pat. No. 3,917,588 and to the 3-halo-3-cephem antibiotics by methods described by U.S. Pat. No. 3,925,372.

Alternatively, the products of the process can be converted to the 3-halo-3-cephem or 3-methoxy-3-cephem derivatives and then N-deacylated to provide the known 3-halo-3-cephem and 3-methoxy-3-cephem nuclei. The latter can be reacylated to provide the desired 7β-acylamino derivative.

The following Preparations and Examples are provided to further describe the present process.

PREPARATION 1

L-α-Aminoadipoyl-L-cysteinyl-D-β,γ-didehydrovaline

N-Benzyloxycarbonyl-α-benzyl-δ-(L-α-amino-adipoyl)-S-benzyl-L-cysteinyl-D-β,γ-didehydrovaline benzyl ester prepared as described by J. E. Baldwin et al., *Tetrahedron*, 1982, 18, 2773–2776, was deprotected as follows.

Ammonia (100 ml) was distilled under argon atmosphere into a 250 ml round-bottomed flask which had been equipped with a dry ice/isopropanol condenser. A small piece of sodium (100 mg) was added and the solution refluxed for 30 minutes. The so dried ammonia (50 ml) was then distilled into a second round-bottomed flask, which contained the protected tripeptide in dry tetrahydrofuran (10 ml). Sodium was added in small pieces until the blue color of the sodium remained. The reaction mixture was left stirring for 10 minutes (solution remaining blue) and the excess sodium quenched with dry $(NH_4)_2SO_4$ (solution colorless). After evaporation of the mixture to dryness by leaving it to stir at room temperature and then by removing the tetrahydrofuran under reduced pressure, the white residue was taken up in 0.2 N sulfuric acid (10 ml).

EXAMPLE 1

An aqueous solution of δ-(L-α-aminoadipoyl)-L-cysteinyl-D-β,γ-didehydrovaline as the disulfide (28 mM, 0.100 ml) was mixed with aqueous solutions of dithiothreitol (100 mM, 0.100 ml), ferrous sulfate (5 mM, 0.100 ml), L-ascorbic acid (50 mM, 0.100 ml), bovine liver catalase (10,000 units/ml, 0.050 ml), and of ammonium bicarbonate (50 mM, 3.5 ml). The pH of the solution was adjusted to 8, when necessary, with 100 mM sodium hydroxide. The solution was shaken at 27° C. for 5 minutes and 1 ml of a solution of isopenicillin N synthetase (5 I.U./ml isolated from *Acremonium crysocenum* CO728, ATCC 74315) in 50 mM ammonium bicarbonate was added. The mixture was shaken at about 27° C. for 45 minutes, the reaction terminated by precipitating the protein with 7 ml of acetone, and the precipitate separated by centrifugation. The supernatant was evaporated in vacuo, and the residue containing the product, (2R,6R,7R)-7-(5S-5-amino-5-carboxypentanamido)-3-exomethylene-8-oxo-(1-aza -5-thiabicyclo[4.2.0]octane), 2-carboxylic acid, was lyophilized.

The 3-exomethylenecepham product was isolated from the residue by reverse phase octadecylsilane HPLC on a 250×4.6 mm column using 10 mM ammonium bicarbonate buffer as the eluant.

NMR: δH (500 MHz, $D_2O$, pH 7, TSP=0.00 p.p.m.), 1.65–1.80, 1.82–1.45 (4H, 2×m, $CH_2CH_2CH_2CO$), 2.41 (2H, t, J=7Hz, $CH_2CO$), 3.37, 3.61 (2H, ABq, J= 14Hz, $C_4H$), 3.74 (1H, dd, J=5.5, 7Hz, $CH(CH_2)_3$), 4.98 (1H, s, $C_2H$), 5.24, 5.28 (2H, 2×s, $CH_2$=), 5.39 (1H, d, J=4Hz, β-lactam-H), 5.42 (1H, d, J=4Hz, β-lactam-H).

The above n.m.r. spectrum of the isolated product was identical to that of its diastereoisomer, 3-exomethylenecephalosporin C having the D-α-aminoadipoyl side chain.

Mass Spectrum (positive argon Fast Atom Bombardment):

m/e 358 (MH⁺).

The connectivities $CH_2$—$C(CH_2)$—CH— were established by a Jenner 20 spectrum (A. Bax, "Two Dimensional Nuclear Magnetic Resonance in Liquids", Reidel, London, 1982). The product was resistant to penicillinase from *Bacillus cereus* in an experiment monitored by direct $^1H$ n.m.r. (500 MHz) observation.

EXAMPLE 2

δ-(L-Carboxymethylcysteinyl)-L-cysteinyl-D,β,γ-didehydrovaline is reacted with IPNS by employing the procedures and conditions described by Example 1 to provide 7β-[L-[(2-amino-2-carboxy)ethylthio]acetamido]-3-exomethylenecepham-4-carboxylic acid.

EXAMPLE 3

7β-Phenoxyacetylamino-3-exomethylenecepham-4-carboxylic acid

Phenoxyacetyl-L-cysteinyl-D-β,γ-didehydrovaline, 1 mg,-is dissolved in 2 ml of 50 mM ammonium bicarbonate and the solution is mixed with 100 μl of a 50 mM ascorbate solution, 100 μl of a 50 mM ferrous sulfate solution, 50 μl of catalase (Sigma, 10%), and 100 μl of a 100 mM solution of dithiothreitol. The mixture is stirred for 10 minutes (pH 7.7) and 2.65 ml of a solution of isopenicillin N synthetase, 5.46 I.U. in 50 mM ammonium bicarbonate, are added. The mixture is shaken at 27° C. at 270 rpm for 25 minutes. The mixture is then diluted with about 10 ml of acetone and the precipitated protein is separated by centrifugation. The title compound is extracted with a water immiscible solvent such as ethyl acetate from the acidified supernatant.

EXAMPLE 4

7β-Phenylacetylamino-3-exomethylenecepham-4-carboxylic acid is obtained by reacting phenylacetyl-L-cysteinyl-D-β,γ-didehydrovaline with IPNS by using the procedures and reagents described by Example 3.

I claim:

1. A process for preparing a compound of the formula wherein:

R is phenoxyacetyl;

or an alkali metal or alkaline earth metal salt thereof; which comprises reacting in an aqueous medium in the presence of oxygen, ferrous ion and ascorbic acid, at a temperature between about 20° C. and about 40° C. and at a pH of between about 6 and about 9, a dipeptide of the formula:

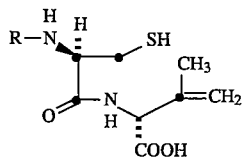

with isopenicillin N synthetase obtained from *Acremonium chrysogenum* CO728, ATCC 74315, and recovering said compound.

2. The process of claim 1 wherein the dipeptide is contacted with isopenicillin N synthetase in the presence of ferrous ion at a concentration between about 50 μM and about 0.2 mM.

3. The process of claim 1 carried out at a pH of about 8 and at a temperature of between about 25° C. and about 30° C.

4. The process of claim 1 carried out in the presence of catalase.

\* \* \* \* \*